United States Patent [19]

Schaar et al.

[11] 4,330,220
[45] May 18, 1982

[54] SCRUB SPONGE

[75] Inventors: Charles H. Schaar, Lake Zurich; Nicholas A. Marra, Glen Ellyn; William J. Dunn, Libertyville; Frank K. Villari, Oak Park, all of Ill.

[73] Assignee: The Kendall Company, Boston, Mass.

[21] Appl. No.: 158,743

[22] Filed: Jun. 12, 1980

[51] Int. Cl.³ .................... B05C 17/00; A61M 35/00
[52] U.S. Cl. .................................. 401/134; 401/196; 128/269
[58] Field of Search ................... 401/132–135, 401/196, 201, 208; 128/269; 206/227; 220/257, 258, 277, 278

[56] References Cited
U.S. PATENT DOCUMENTS

| | | | |
|---|---|---|---|
| 2,911,664 | 11/1959 | Zecchini | 401/132 |
| 3,066,347 | 12/1962 | Vosbikian et al. | 401/201 |
| 3,172,478 | 3/1965 | Giclas | 220/278 |
| 3,485,562 | 12/1969 | Hidden et al. | 401/134 |
| 3,636,922 | 1/1972 | Ketner | 401/132 |
| 3,774,609 | 11/1973 | Schwartzman | 128/269 |
| 4,027,985 | 6/1977 | Loesser | 401/134 |
| 4,117,841 | 10/1978 | Perrotta et al. | 401/132 |
| 4,148,318 | 4/1979 | Meyer | 401/134 |
| 4,240,760 | 12/1980 | Levine | 401/201 |
| 4,291,697 | 9/1981 | Georgevich | 401/132 |

FOREIGN PATENT DOCUMENTS 1161656 9/1958 France ........................ 401/134

Primary Examiner—William Pieprz
Attorney, Agent, or Firm—Powell L. Sprunger

[57] ABSTRACT

A scrub sponge comprising, a packet having a rupturable wall and a closed chamber containing a liquid scrub agent, and a cover of foam material having a cavity to receive the packet. The sponge has a puncture member intermediate the cover and the rupturable wall, with the puncture member having a projection facing toward the puncturable wall such that the projection pierces the puncturable wall when the puncture member is pressed toward the packet to release the scrub agent into the cover.

18 Claims, 5 Drawing Figures

U.S. Patent May 18, 1982 4,330,220
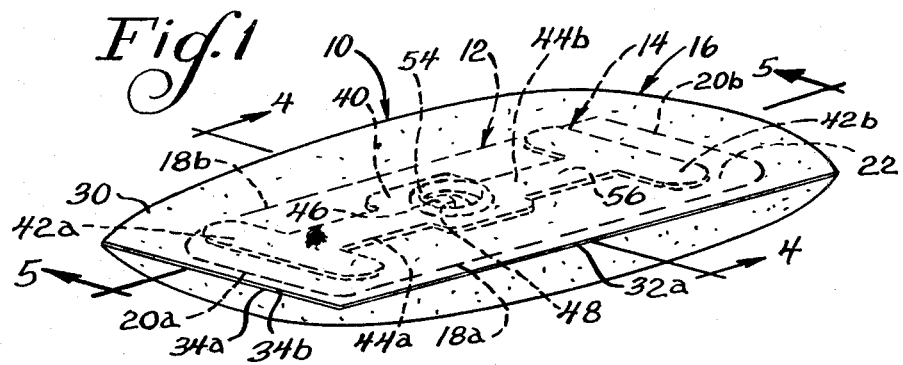
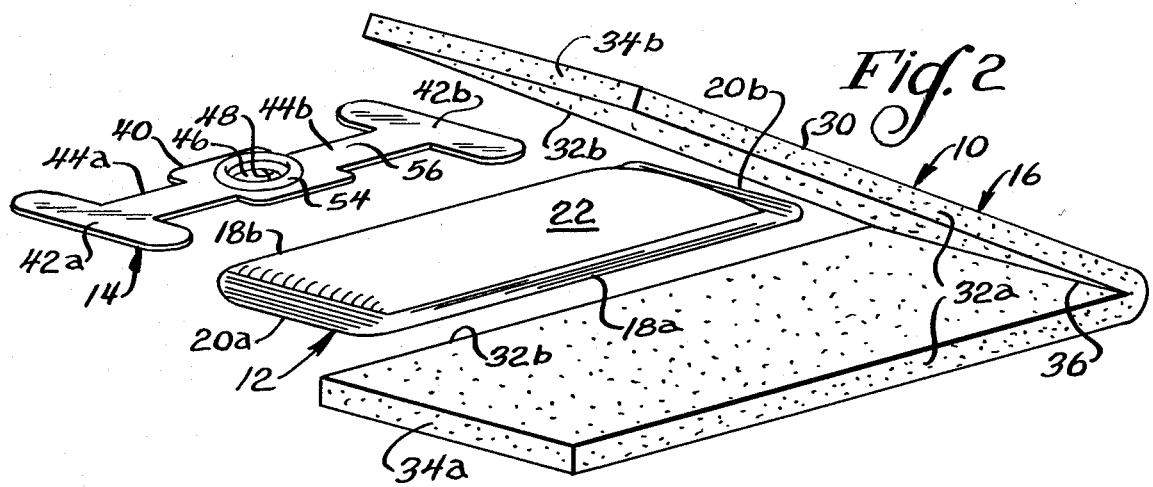
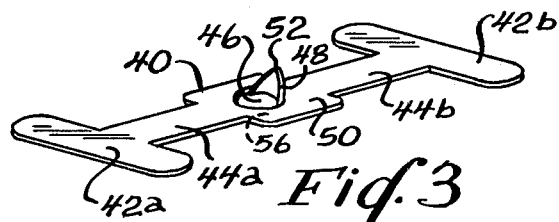
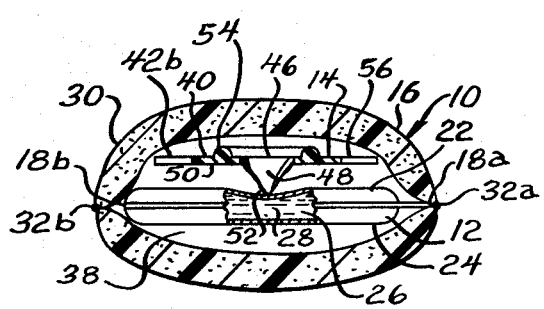
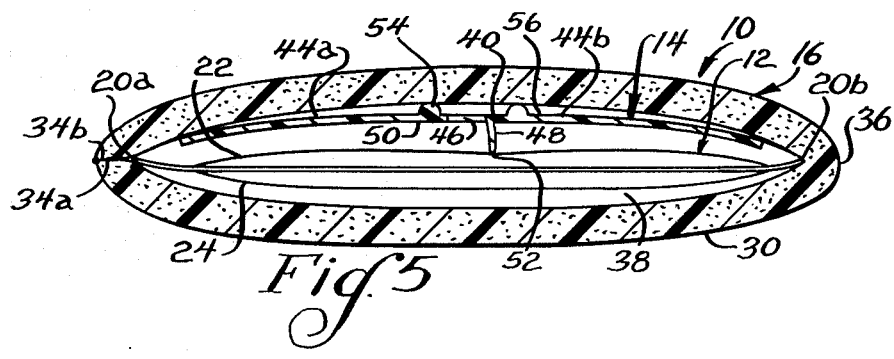

SCRUB SPONGE

BACKGROUND OF THE INVENTION

The present invention relates to surgical devices, and more particularly to scrub sponges.

Prior to surgery, the operative site is cleaned by hospital personnel in order to minimize the possibility of contamination around the site. First, a scrub solution comprising a soap or detergent is utilized to wash the patient in the region of the operative site after which the scrub solution is removed from the patient. Next, the patient is painted with an antiseptic liquid, such as povidone iodine, in the region of the site. When dry the antiseptic paint provides a continuous protective film in the region of the site, and surgery is ready to commence.

In the past, applicators, such as sponges, have been impregnated with the detergent and antiseptic liquid, which have been retained separate from the sponges, in order to accomplish the scrub procedure. However, it is desirable to facilitate handling of the scrub materials in order to maximize convenience to the hospital personnel and minimize the possibility of contamination during the procedure.

SUMMARY OF THE INVENTION

A principal feature of the present invention is the provision of an improved sponge for scrubbing procedures.

The scrub sponge of the present invention comprises, a packet having a rupturable wall and a closed chamber containing a liquid scrub agent. The sponge has a cover of foam material having a cavity to receive the packet. The sponge also has a puncture member intermediate the cover and the rupturable wall, with the puncture member having a projection facing toward the puncturable wall.

A feature of the present invention is that the projection pierces the puncturable wall when the puncture member is pressed toward the packet.

Another feature of the invention is that the pierced wall releases the scrub agent from the packet.

Still another feature of the invention is that the puncture member has an opening to permit passage of the released scrub agent into the cover.

Yet another feature of the invention is that the cover retains the scrub agent in a position for easy placement on the patient.

Thus, a feature of the present invention is that the scrub agent may be released and applied to the patient in a simplified manner.

Further features will become more fully apparent in the following description of the embodiments of this invention and from the appended claims.

DESCRIPTION OF THE DRAWINGS

In the drawings:

FIG. 1 is a perspective view of a scrub sponge of the present invention;

FIG. 2 is an exploded view of the scrub sponge of FIG. 1;

FIG. 3 is a perspective view of a puncture member for the sponge of FIG. 1;

FIG. 4 is a sectional view taken substantially as indicated along the line 4—4 of FIG. 1; and FIG. 5 is a sectional view taken substantially as indicated along the line 5—5 of FIG. 1.

DESCRIPTION OF THE PREFERRED EMBODIMENTS

Referring now to FIGS. 1-5, there is shown a scrub sponge generally designated 10 having a packet 12, a puncture member 14, and a cover 16. The packet 12 has a pair of side edges 18a and 18b, and a pair of end edges 20a and 20b connecting the side edges 18a and b. The packet 12 has a front wall 22 and a back wall 24 which are joined at their periphery to define a chamber 16 intermediate the front and back walls 22 and 24. The front and back walls 22 and 24 are made from a puncturable material, such as a lamination of metallic foil and heat sealable plastic, such that the edges of the front and back walls 22 and 24 may be heat sealed together to form the chamber 26. The packet 12 contains a liquid scrub agent 28 in the chamber 26, such as a solution of soap or detergent, or a solution containing an antiseptic agent, such as povidone iodine.

The cover 16 preferably comprises an absorbent and porous foam material, such as polyurethane foam. In a preferred form, the cover 16 comprises an elongated strip 30 having a pair of side edges 32a and 32b, and a pair of end edges 34a and 34b connecting the side edges 32a and b. The strip 30 is folded about a fold line 36 at a longitudinal central portion of the strip, such that the end edges 34a and 34b are located adjacent each other when the strip 30 is folded. The side edge 32a of the strip 30 intermediate fold line 36 and the end edges 34a and b are joined together by suitable means, such as by heat sealing, the side edge 32b intermediate the fold line 36 and the end edges 34a and b are joined together by suitable means, such as by heat sealing, and the end edges 34a and b are joined together by suitable means, such as by heat sealing. In this manner, the joined edges of the strip 30 define a cavity 38 to receive the packet 12, with the width of the packet between the side edges 18a and b being approximately equal to the width of the cavity 38, and with the length of the packet 12 intermediate the end edges 20a and b being approximately equal to the length of the cavity 38. In this configuration, the side edge 18a of the packet 12 is located adjacent the side edge 32a of the cover 16, the side edge 18b of the packet 12 is located adjacent the side edge 32b of the cover 16, the end edge 20a of the packet 12 is located adjacent the joined end edges 34a and b of the cover 16, and the end edge 20b of the packet 12 is located adjacent the fold line 36 of the cover 16.

The puncture member 14 has a central portion 40, a pair of laterally extending wings 42a and 42b adjacent opposed ends of the puncture member 14, and a pair of longitudinal extensions 44a and 44b connecting the central portion 40 to the wings 42a and b. The central portion 40 has an opening 46 extending through the puncture member 14, and a projection 48 extending from one face 50 of the puncture member 14 adjacent the opening 46. The projection 48 is tapered in order to define a relatively sharp point 52 extending from the puncture member 14. The puncture member 14 has a raised ring 54 extending around the opening 46 on the other face 56 of the puncture member 14, such that the ring 54 is located in the region of the projection 48. In a preferred form, the puncture member may be formed from a flexible plastic material, such as polypropylene.

As shown, the puncture member 14 is received in the cover cavity 38 at a location intermediate the puncturable wall 22 and the cover 16. The width of the wings 42a and b is approximately equal to the width of the cover cavity 38, and the length of the puncture member 14 between the wings 42a and b is approximately equal to the length of the packet 12, such that the wings 42a and b of the puncture member 14 retain the puncture member in place in the cavity 38 in a configuration with the central portion 40 and projection 48 overlying the front wall 22 of the packet 12.

In use, the sponge 10 is grasped by the user's hands, and the fingers are utilized to locate the enlarged ring 54 through the cover 16 which indicates the location of the projection 48. Next, the puncture member 14 is pressed by squeezing the cover 16 in the region of the ring 54 in order to push the projection 48 through the front wall 22 of the packet 12. As the projection 48 pierces the front wall 22 of the packet 12 and the sponge 10 is squeezed, the scrub liquid passes through the puncture in the wall 22 and through the opening 46 in the puncture member 14 into the absorbent cover 16 where the liquid is retained preparatory to use. Next, the wetted cover 16 may be applied to the patient in order to introduce the scrub liquid onto the skin of the patient. The sponge may be squeezed an additional amount in order to introduce additional liquid from the packet 12 to the cover 16 in a position for application to the patient. As previously discussed, the packet 12 may contain a detergent solution in which case the sponge 10 may be utilized to initially cleanse the patient's skin about the operative site. A separate sponge 10 may have a packet 12 which retains an antiseptic agent, such as povidone iodine, and the separate sponge may be utilized to paint the region of the patient about the operative site after cleansing.

Thus, in accordance with the present invention, the scrub sponge 10 may be simply squeezed in order to release a scrub liquid onto the outer cover of the sponge. After the packet 12 has been pierced and squeezed, the cover 16 of the sponge 10 may be utilized to apply the scrub liquid onto the patient's skin. Thus, the sponge of the present invention permits application of the scrub liquid in a simplified manner to the patient.

The foregoing detailed description is given for clearness of understanding only, and no unnecessary limitations should be understood therefrom, as modifications will be obvious to those skilled in the art.

We claim:

1. A scrub sponge, comprising:
   a packet having a rupturable wall and a closed chamber containing a liquid scrub agent;
   a cover of foam material having a cavity to receive said packet and completely enclosing said packet; and
   a puncture member intermediate said cover and the rupturable wall, with the puncture member having a projection facing toward the puncturable wall such that the projection pierces the puncturable wall when the puncture member is pressed toward said packet to release said scrub agent into the cover, said projection being located adjacent a longitudinal central portion of the puncture member, in which the puncture member has a pair of laterally extending wings adjacent opposed ends of the puncture member, and in which the puncture member has a pair of longitudinal extensions connecting said wings and said central portion of the puncture member.

2. The sponge of claim 1 wherein said cover comprises an elongated sheet having a pair of opposed side edges and a pair of opposed end edges connecting the side edges, with said sheet being folded along a line at a longitudinal central portion of the sheet intermediate said end edges, said side edges intermediate the fold line and end edges being joined together, and said end edges being joined together to define the cavity.

3. The sponge of claim 2 wherein said packet has a pair of opposed side edges, and a pair of opposed end edges connecting the side edges, with one of the packet end edges being located adjacent the joined end edges of the cover, with the other packet end edge being located adjacent the cover fold line, and with the packet side edges being located adjacent the joined side edges of the cover.

4. The sponge of claim 1 wherein said cover comprises a polyurethane foam.

5. The sponge of claim 1 wherein the walls of said packet comprise a metallic foil.

6. The sponge of claim 1 wherein said scrub agent comprises povidone iodine.

7. The sponge of claim 1 wherein said scrub agent comprises a detergent.

8. The sponge of claim 1 wherein said puncture member has a length substantially the length of said packet.

9. The sponge of claim 1 wherein said puncture member has a width substantially the width of said cavity.

10. The sponge of claim 1 wherein said puncture member comprises a flexible plastic material.

11. The sponge of claim 1 wherein said puncture member has an enlargement facing said cover in the region of said projection.

12. The sponge of claim 1 wherein said projection is tapered toward a relatively sharp point.

13. The sponge of claim 1 wherein said puncture member has a puncture portion with an opening extending through said puncture member, and with said projection being located adjacent said opening.

14. The sponge of claim 13 wherein said puncture member includes a raised ring surrounding said opening on a side of the puncture member facing said cover.

15. The sponge of claim 13 wherein said puncture portion is located adjacent a longitudinal central portion of the puncture member.

16. The sponge of claim 1 wherein said wings have a length substantially the width of the cover cavity.

17. The sponge of claim 1 wherein said packet has a width and length substantially the width and length of said cavity.

18. A scrub sponge, comprising:
   a packet having a rupturable wall and a closed chamber containing a liquid scrub agent;
   a cover of foam material having a cavity to receive said packet and completely enclosing said packet, said cavity having a width and length approximately the dimensions of the cover; and
   a puncture member intermediate said cover and the rupturable wall, with the puncture member having a projection facing toward the puncturable wall such that the projection pierces the puncturable wall when the puncture member is pressed toward said packet to release said scrub agent into the cover, said puncture member having a width and length substantially the width and length of the cavity, said projection being located adjacent a longitudinal central portion of the puncture member, in which the puncture member has a pair of laterally extending wings adjacent opposed ends of the puncture member, and in which the puncture member has a pair of longitudinal extensions connecting said wings and the central portion of the puncture member, said wings having a length substantially the width of the cavity.

* * * * *